United States Patent [19]

Brossi et al.

[11] Patent Number: 4,533,675
[45] Date of Patent: Aug. 6, 1985

[54] CARBAMATES OF COLCHICINE FOR TREATMENT OF GOUT

[75] Inventors: Arnold Brossi; Peter Kerekes, both of Bethesda, Md.

[73] Assignee: The United States of America as represented by the Department of Health and Human Services, Washington, D.C.

[21] Appl. No.: 601,314

[22] Filed: Apr. 17, 1984

[51] Int. Cl.³ .............. C07C 125/065; C07C 125/067; A61K 31/24
[52] U.S. Cl. .................... 514/480; 560/28; 560/10
[58] Field of Search ............... 560/28, 10; 424/309; 514/480

[56] References Cited

PUBLICATIONS

Goodman and Gilman's, The Pharmacological Basis of Therapeutics, 6th ed., (1980), 718.
Raffauf et al., Jour. Amer. Chem. Soc., vol. 75, (1953), 5292-5294.
Capraro et al., Helv. Chim. Acta, vol. 62, (1979), 965-970.
Velluz et al., Bull. Chim. Soc. Fr., (1954), 1072-1075; 194-197.
Roche, Design of Biopharmaceutical Properties through Prodrugs and Analogs, (1977), 234.

Primary Examiner—Bernard Helfin
Attorney, Agent, or Firm—John S. Roberts, Jr.

[57] ABSTRACT

The present invention consists of derivatives of colchicine and thiocolchicine which are carbamates of the same and are illustrated by the formula below:

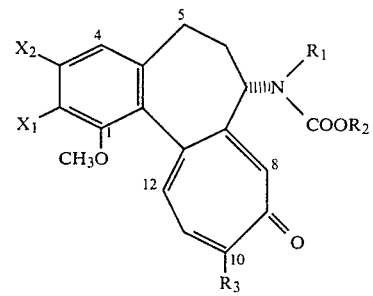

where either $X_1$ or $X_2$ is a hydroxy group and the other a lower alkoxy group and $R_1$ can be H or an alkyl, $R_2$ an alkyl, alkenyl or aryl which may be substituted and $R_3$ is either $OCH_3$ or $SCH_3$; alkyl and alkoxy=$C_1$-$C_6$; aryl=monoaryl.

These compounds are not only new but have exhibited antitumor activity binding to tubulin protein and tests against P388 lymphocytic leukemia and also active against gouty arthritis. Further, they are far less toxic than colchicine.

5 Claims, No Drawings

CARBAMATES OF COLCHICINE FOR TREATMENT OF GOUT

The present invention consists of derivatives of colchicine and thiocolchicine which are carbamates of the same and are illustrated by the formula below:

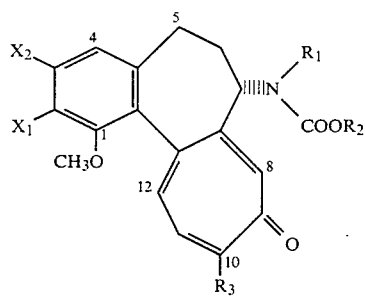

where either $X_1$ or $X_2$ is a hydroxy group and the other a lower alkoxy group and $R_1$ can be H or an alkyl, $R_2$ an alkyl, alkenyl or aryl which may be substituted and $R_3$ is either $OCH_3$ or $SCH_3$; alkyl and alkoxy=$C_1$-$C_6$; aryl=monoaryl.

These compounds are not only new but have exhibited antitumor activity binding to tubulin protein and tests against P388 lymphocytic leukemia and also active against gouty arthritis. Further, they are far less toxic than colchicine.

The present application describes certain colchicine and thiocolchicine derived N-carbamates which are potent antileukemic and antigout agents with lesser toxicity than the parent alkaloids.

The powerful effects of colchicine on cell division is well-known in the literature, see Goodman and Gilman's *The Pharmacological Basis of Therapeutics*, 6 edition, MacMillan Publishing, 1980, page 718.

Colchicine inhibits cell processes which depend on microtubule function because it binds almost irreversibly to the subunit tubulin and blocks its polymerization. The binding to tubulin is responsible for the anti-gout effect, the only therapeutic use recommended for colchicine. The powerful antimitotic effect of colchicine practically forbids its use in the treatment of cancer because colchicine, as well as its congeners, is too toxic.

The starting amines deacetylcolchicine, deacetylthiocolchicine, demecolcine and thiodemecolcine are available from the alkaloid colchicine and its methylmercapto analog thiocolchicine by well established procedures. They react with chloroformate in the presence of base, preferably triethylamine, to afford the above-mentioned carbamates as crystalline compounds.

The carbamates bind well to microtubule protein in vitro, have excellent activity in lymphocytic leukemia P388 screen in mice, and are considerably less toxic than colchicine or demecolcine in mice. These carbamates are improved drugs with the mode of action of colchicine.

The high toxicity of colchicine and thiocolchicine is well known and, as above noted, practically forbids the use of these drugs for the treatment of cancer and for gout only under a doctor's supervision.

The carbamates described in this invention are less toxic in the animal screening, bind to tubulin protein in vitro, and are potent antitumor agents in the lymphocytic leukemia P388 assay. It can be seen from the table below that the carbamates behave in the screening similarly as the parents but are at the same time 10 to 30-times less toxic.

TABLE

| $R_1$ | $R_2$ | $R_3$ | $LD_{50}$ in Mice after ip inj in mg/kg | Tubulin Binding in vitro |
|---|---|---|---|---|
| Ph | H | SMe | 50 | — |
| Et | H | SMe | 77.1 | 96 |
| Et | H | OMe | 114 | 86 |
| Colchicine* | | | 3.0 | 90 |
| Thiocolchicine* | | | 0.32 | 90 |

*Data from Brossi et al., J. Med. Chem., 26:1365 (1983).

The preparation of the deacetylcolchicine required for the derivatization has been made by Raffauf et al., *J. Amer. Chem. Soc.*, 75:5292 (1953) from deacetylcolchicine, also called trimethylcolchicinic acid (1) through O-methylation. In this step 2 tautomeric O-methyl ethers, deacetylcolchicine (2) and deacetylisocolchicine (3) are formed, which can be separated or used directly as mixture. Another modus of preparation of deacetylcolchicine (2) was described by Capraro et al., *Helv. Chim. Acta*, 62:965 (1979).

An example using a mixture of 2 and 3 is given in Example 1 (Scheme 1). Reaction of a mixture of 2 and 3 with ethylchloroformate in the presence of a base, such as triethylamine, afforded a mixture of carbamates 4 and 5 which could be separated by chromatography. The slower moving iso-compound 3 can later be hydrolyzed with acid to afford N-ethoxycarbonyl-deacetylcolchicine (6), which can be remethylated to a mixture of 4 and 5.

Scheme 2 shows the preferred method for the synthesis of carbamates of the colchicine and thiocolchicine series, reacting deacetylthiocolchicine, readily available from thiocolchicine by the method of Velluz et al., *Bull. Chim. Soc. Fr.*, 1072 (1954), with chloroformates in the presence of a base, such as triethylamine.

Scheme 3 shows an example of the demecolcine family of compounds, which can similarly be obtained by reaction of the amines with chloroformates in the presence of a cosolvent such as benzene and a base such as triethylamine or potassium carbonate.

Since iso-compounds are biologically not active as antitumor or antigout agents, they have to be separated if they are formed but can be reconverted into useful intermediates as mentioned above.

SCHEME 1

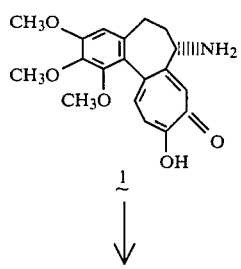

-continued
SCHEME 1

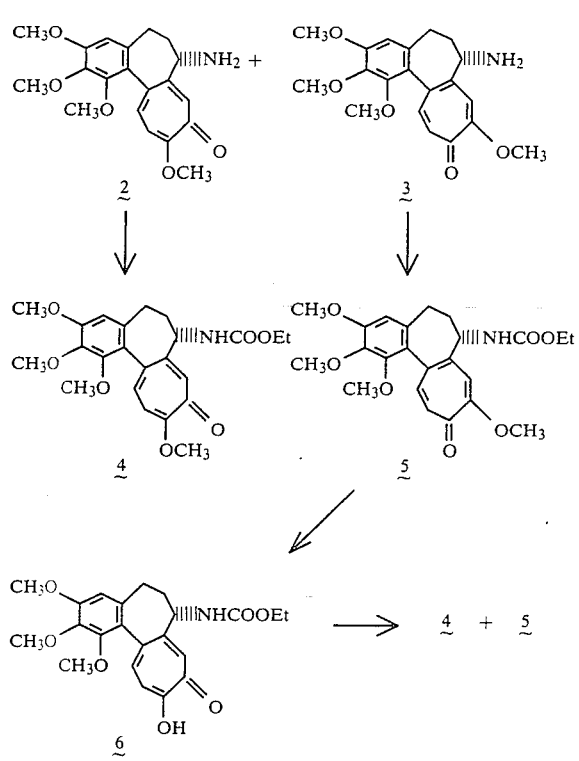

SCHEME 2

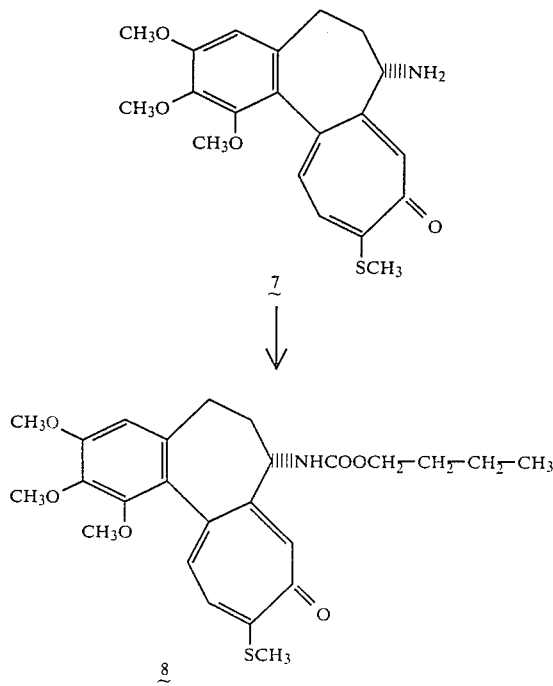

SCHEME 3

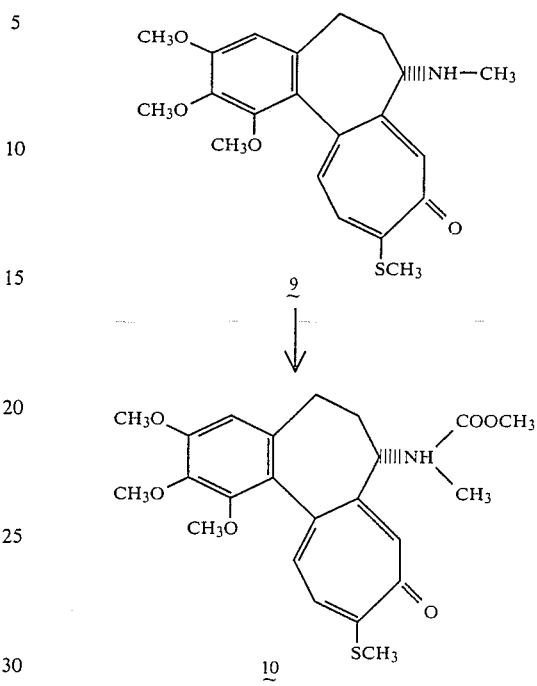

EXAMPLE 1

N-Ethoxycarbonyl-deacetylcolchicine 1 g of a mixture of deacetylcolchicine (2) and deacetylisocolchicine (3), prepared by the method of Raffauf et al., *J. Amer. Chem. Soc.*, 75:5292 (1953), was dissolved in 20 ml methylene chloride, cooled with ice, and added with 0.6 ml triethylamine and 0.5 ml ethylchloroformate. After stirring at room temperature for 24 hr. and dilution with water, the organic phase was separated and the aqueous phase extracted several times with methylene chloride. The combined methylene chloride extracts were dried with $Na_2SO_4$, evaporated, and the residue chromatographed on a silica-gel column packed with chloroform. The material was eluted with chloroform containing 2.5% methanol and 0.5% ammonia. The N-ethoxycarbonyl-deacetylcolchicine (4) eluted first was crystallized from ethylacetate/methanol, affording crystals of mp 209°-211°, $[\alpha]_D = 173°$ ($CHCl_3$).

The second compound isolated was N-ethoxycarbonyl-deacetylisocolchicine (5) of mp 202°-203°, $[\alpha]_D = -249°$ ($CHCl_3$).

N-Ethoxycarbonyl-deacetylisocolchicine (5), when heated with methanolic HCl (10 ml MeOH and 10 ml 0.2N HCl) for 10 hr. under reflux, afforded, after cooling and standing, the N-ethoxycarbonyl-deacetylcolchicine (6) mp 172°-173°, $[\alpha]_D = -149°$ which, after O-methylation with etherial diazomethane, or with methyl iodide in appropriate solvents such as acetone, afforded a mixture of 4 and 5 which could be separated by chromatography, thus getting another amount of the biologically active material 4.

EXAMPLE 2

N-Phenoxycarbonyl-deacetylthiocolchicine 1 g of Deacetylthiocolchicine (7), prepared by acid hydrolysis of thiocolchicine according to the method of L. Velluz and G. Muller, *Bull. Soc. Chim. Fr.*, 1072 (1954), was reacted with 3 ml of phenylchloroformate and 3 ml of triethylamine for 2 hr at 50°, afforded after usual workup the N-phenoxycarbonyl-deacetylthiocolchicine (8) of mp 152°, $[\alpha]_D = -219°$ (CHCl$_3$).

EXAMPLE 3

Prepared according to Example 2 were the N-butoxycarbonyl-deacetylthiocolchicine of mp 180°-2° C. $[\alpha]_D = -217.2$ (CHCl$_3$) and N-methoxycarbonyl-thiodemecolcine. 1 g of thiodemecolcine (9), prepared from deacetylthiocolchicine by the method used by H. G. Capraro and A. Brossi, *Helv. Chim. Acta*, 62:965 (1979), in the colchicine series, when reacted with 0.6 ml methylchloroformate in 0.6 ml triethylamine similarly afforded the carbamate (10), mp 161°-3° C., $[\alpha]_D = -312.5°$ (CHCl$_3$).

EXAMPLE 4

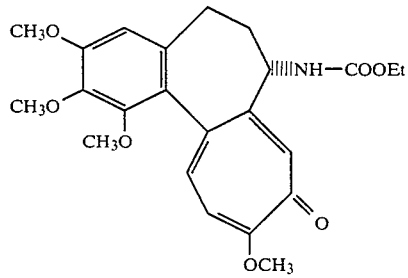

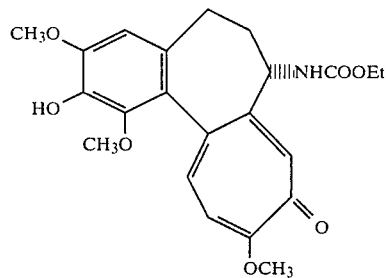

344 mg N-carbethoxy-deacetylcolchicine was dissolved in 5 ml conc. sulfuric acid and left at 50°–60° for 4 hr. After pouring on ice and neutralizing the acidic solution with ammonia, the phenolic material was extracted with chloroform and purified by chromatography on silica gel. The material eluted with CHCl$_3$:MeOH=9:1 was 2-demethyl-N-carbethoxy-deacetylcolchicine of m.p. 273°–274°, $[\alpha]_D^{22} = -177°$ (C 0.22, CHCl$_3$).

We claim:

1. A compound of the colchicine and thiocolchicine series according to the following formula

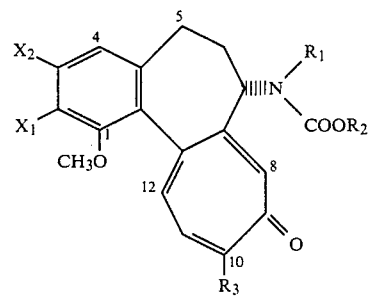

where either $X_1$ or $X_2$ is a hydroxy group and the other a lower alkoxy group and $R_1$ can be H or an alkyl, $R_2$ an alkyl, alkenyl or aryl which may be substituted and $R_3$ is OCH$_3$; alkyl and alkoxy=C$_1$-C$_6$; aryl=monoaryl.

2. A compound according to claim 1 wherein $R_3$=SCH$_3$, $R_1$=H, and $R_2$=—CH=CH$_2$.

3. N-Ethoxycarbonyl-deacetylcolchicine.

4. 2-Demethyl-N-carbethoxy-deacetylcolchicine.

5. The method of treating gouty arthritis in mice which comprises injecting intraperitoneally per diem up to 20 mg/kg of a compound of the formula of claim 1.

* * * * *